(12) United States Patent
Miri

(10) Patent No.: US 12,102,378 B2
(45) Date of Patent: Oct. 1, 2024

(54) ELECTROSURGICAL HANDPIECE WITH ACCURATE TISSUE SENSING

(71) Applicant: Medtronic Advanced Energy LLC, Minneapolis, MN (US)

(72) Inventor: Mohammad Miri, Longmount, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 542 days.

(21) Appl. No.: 17/301,597

(22) Filed: Apr. 8, 2021

(65) Prior Publication Data

US 2022/0323138 A1 Oct. 13, 2022

(51) Int. Cl.
| A61B 18/14 | (2006.01) |
| A61B 18/16 | (2006.01) |
| A61B 18/00 | (2006.01) |
| A61B 18/12 | (2006.01) |

(52) U.S. Cl.
CPC .......... *A61B 18/1402* (2013.01); *A61B 18/16* (2013.01); *A61B 2018/00589* (2013.01); *A61B 2018/0063* (2013.01); *A61B 2018/00827* (2013.01); *A61B 2018/00845* (2013.01); *A61B 18/1206* (2013.01); *A61B 2018/1273* (2013.01); *A61B 2018/128* (2013.01)

(58) Field of Classification Search
CPC .......... A61B 2018/00827; A61B 2018/00845; A61B 2018/1273; A61B 18/1402; A61B 18/16; A61B 18/1206; A61B 2018/128
See application file for complete search history.

(56) References Cited

U.S. PATENT DOCUMENTS

| 6,558,385 | B1 | 5/2003 | McClurken et al. |
| 6,702,810 | B2 | 3/2004 | McClurken et al. |
| 6,953,461 | B2 | 10/2005 | McClurken et al. |
| 7,115,139 | B2 | 10/2006 | McClurken et al. |
| 7,645,277 | B2 | 1/2010 | McClurken et al. |
| 2014/0253140 | A1* | 9/2014 | Gilbert ............... A61B 18/1206 324/527 |
| 2017/0090507 | A1* | 3/2017 | Wiener ............... A61B 18/1445 |
| 2019/0274716 | A1* | 9/2019 | Nott ..................... A61B 17/295 |

OTHER PUBLICATIONS

Medtronic, Inc., "Monopolar Sealers", https://www.medtronic.com/us-en/healthcare-professionals/products/general-surgery/electrosurgical/monopolar-hemostatic-sealers.html, accessed on Jul. 7, 2021, 6 pgs.
Medtronic, Inc., "Aquamantys™ M Bioplar Sealers", https://www.medtronic.com/us-en/healthcare-professionals/products/general-surgery/electrosurgical/aquamantys-bipolar-sealers.html, accessed on Jul. 7, 2021, 10 pgs.

* cited by examiner

*Primary Examiner* — Michael F Peffley
*Assistant Examiner* — Samantha M Good
(74) *Attorney, Agent, or Firm* — Husch Blackwell LLP

(57) ABSTRACT

Systems described herein include a two-tip handpiece that delivers current from two sources at two different frequencies. Signals at different frequencies are absorbed differently in the body. Accordingly, both monopolar and bipolar systems using this two-tip handpiece and dual-frequency signal can detect impedance (or other frequency-dependent characteristics) of the target tissue at the tips while delivering treatment, which was not possible or practical using conventional systems.

8 Claims, 4 Drawing Sheets

ELECTROSURGICAL HANDPIECE WITH ACCURATE TISSUE SENSING

FIELD

The present technology is generally related to radio frequency electrosurgery. Application of electrical heating can create coagulation to heal vessels or tissue bleeding.

BACKGROUND

Radio frequency electrosurgery can be used for a variety of applications. Ablation, sealing, cauterizing, and other functions can be accomplished by directing electrical signal through a patient at an appropriate frequency, current level, and amplitude.

For example, rapid sealing of bleeding vessels is useful in a number of procedures, and has applications in various fields such as orthopaedics, spine treatments, oncology, neurosurgery, thoracic surgery, and cardiac implantable electronic devices. Electrosurgery typically uses high-frequency electrical current (e.g., about 200 kHz to about 3.3 MHz), which is above the range that will cause nerve or muscle stimulation.

Existing electrosurgical devices include the AQUAMANTYS™ bipolar and monopolar handheld systems that are commercially available from the applicant, Medtronic. The AQUAMANTYS™ devices use a combination of radiofrequency (RF) energy and saline to provide electrosurgical treatments. In one example, these systems can be used for hemostatic sealing of soft tissue and bone during surgery.

Electrosurgical treatments can involve healing of bleeding vessels using either of two modalities, generally referred to as monopolar and bipolar treatments.

Monopolar electrosurgical devices operate by routing voltage from an active circuit to a handpiece that includes a single tip. The tip emits signal through the tissue to be treated, and charge is collected at a return pad that completes the circuit through the patient's body. In some procedures the patient can lie upon the return pad during treatment. Treatments can be tailored by changing the frequency or voltage of the active circuit, or by changing the position of the tip, or by use of fluid such as saline as described in the applicant's commonly owned patents U.S. Pat. Nos. 6,558,385, 6,702,810, 6,953,461, 7,115,139, and 7,645,277. Use of saline flow around an RF probe to improve effectiveness of coagulation and tissue sealing is a part of many MEDTRONIC® TRANSCOLLATION® devices and surgical procedures. In other uses, monopolar devices can be used for other purposes such as cutting, coagulating, or desiccating the tissue.

Bipolar sealers also deliver electrical signal and, optionally, saline or other fluid, but do so in a different manner. In a bipolar system, rather than a single tip the handpiece includes two tips. Because current can travel between the two tips of the handpiece, no return pad is needed in operation of a bipolar system.

Bipolar and monopolar systems are used in different procedures depending on the objective to be accomplished. A primary consideration is the desired current path. Current in a bipolar system typically follows a shallow path near the tips of the handpiece, whereas current in a monopolar system travels between the tip of the handpiece and the return pad, which is often a longer, deeper current path.

Each of these modalities, monopolar and bipolar, presents a unique benefit. For monopolar systems, the current passes through the entire tissue between a monopolar electrode and a return pad, and the treatment occurs in a region where the current is sufficiently dense (typically near the tip of the handheld device). In a monopolar system, however, there is no way to determine the impedance of individual tissues in the treatment region. For bipolar systems, the impedance of the top region of the tissue (that is, the portion adjacent the bipolar handpiece) can be determined easily, but the accuracy of measurement is limited. Currently, no system exists that provides high accuracy bipolar tissue sensing while delivering the bipolar or monopolar energy.

SUMMARY

The techniques of this disclosure generally relate to improvements in electrosurgical devices that facilitate simultaneous treatment and impedance detection.

In one aspect, the present disclosure provides an electrosurgery system comprising an electrosurgical unit (ESU). The ESU includes a first signal generator configured to generate an electrical signal at a first frequency, a second signal generator configured to generate an electrical signal at a second frequency, and a diplexer configured to combine the electrical signal generated by the first signal generator and the electrical signal generated by the second signal to create a combined signal. The system also includes a handpiece having two tips, the handpiece electrically coupled to the diplexer to deliver the combined signal to at least one of the two tips. The system also includes a return pad, a first current sensing circuit configured to measure a quantity of the electrical signal at the first frequency at the return pad; and a second current sensing circuit configured to measure a quantity of the electrical signal at the second frequency at the other of the other one of the at least two tips.

The electrosurgery system can further include a processor configured to receive a sensed current from each of the first current sensing circuit and the second current sensing circuit. The processor can be configured to modify a power level of the first signal generator based on the sensed current from each of the first current sensing circuit and the second current sensing circuit. The first current sensing circuit and the second current sensing circuit can each be a part of the ESU.

According to another embodiment, an electrosurgery system includes an ESU that again includes a first signal generator configured to generate an electrical signal at a first frequency, a second signal generator configured to generate an electrical signal at a second frequency, and a diplexer configured to combine the electrical signal generated by the first signal generator and the electrical signal generated by the second signal generator to create a combined signal. The system again includes a handpiece including two tips, the handpiece electrically coupled to the diplexer to deliver the combined signal to at least one of the two tips. Additionally, the system includes a diplexer coupled to the other of the at least two tips, a first current sensing circuit configured to measure a quantity of the electrical signal at the first frequency at the other of the at least two tips, and a second current sensing circuit configured to measure a quantity of the electrical signal at the second frequency at the other of the at least two tips.

The electrosurgery system can further include a processor configured to receive a sensed current from each of the first current sensing circuit and the second current sensing circuit. The processor can be configured to modify a power level of the first signal generator based on the sensed current from each of the first current sensing circuit and the second current sensing circuit. The first current sensing circuit and the second current sensing circuit can each be a part of the ESU.

According to another embodiment, a method for providing electrosurgery includes producing a first signal having a first frequency, producing a second signal having a second frequency, combining the first signal and the second signal to form a combined signal, delivering the signal from a handpiece having two tips to a target, collecting a first sensed signal at the first frequency that has traveled through the target along a first path, collecting a second sensed signal at the second frequency that has traveled through the target along a second path, and adjusting a power of the first signal based on a power of the first sensed signal and a power of the second sensed signal.

In some embodiments of the method, the first path is the same as the second path. In such embodiments, the first path and the second path can both extend from one of the two tips to the other of the two tips.

In other embodiments, the first path is different from the second path. In such embodiments, the first path can extend between one of the two tips to a return pad, and the second path can extend between the one of the two tips and the other of the two tips.

In some embodiments, adjusting the power of the first signal comprises estimating an impedance of the target at a region adjacent the two tips and adjusting the power of the first signal based on the impedance. Collecting the first sensed signal at the first frequency that has traveled through the target along the first path and collecting the second sensed at the second frequency that has traveled through the target along the second path can include: applying a first band pass filter along the first path around the first frequency; and applying a second band pass filter along the second path around the second frequency. The first band pass filter and the second band pass filter need not have overlapping frequency ranges.

The details of one or more aspects of the disclosure are set forth in the accompanying drawings and the description below. Other features, objects, and advantages of the techniques described in this disclosure will be apparent from the description and drawings, and from the claims.

Figure 1:
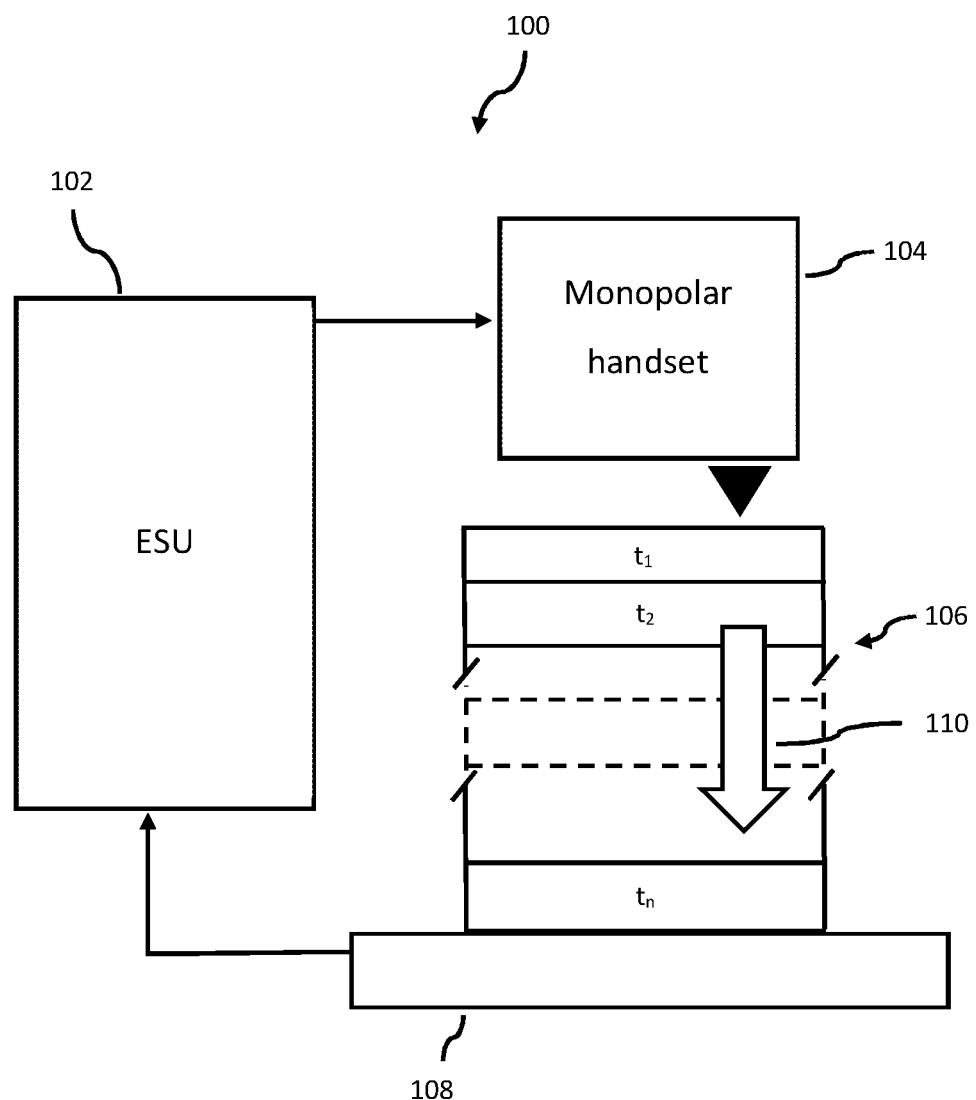
FIG. 1 is a prior art figure of a monopolar electrosurgical system.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Systems and methods described herein accomplish the benefits of both monopolar and bipolar systems in conjunction with one another. Specifically, systems described herein can be used for treatment in both bipolar and monopolar modes, while providing information regarding the impedance of the body. This combination is accomplished through the delivery of multiple frequencies of electrical signal to the body and using a diplexer or similar band pass filtering systems to separate the signal that is returned. The signal delivered to the body can be provided at two frequencies that are particularized for treatment and sensing, respectively.

Throughout this application, the terms "current" and "signal" are both used. The term "current" refers to the conventional meaning of a quantity of charge per cross-sectional area. "Signal" is a broader term that refers generally to information-containing phenomena. "Signal" can, in the broad sense, come in a variety of forms (such as optical, electrical, acoustic, or others). Throughout this application, signals are described that are information conveyed via current. The signal aspects of this current can be the frequency, amplitude, or other features of the electrical current that encode information. For example, a current may be provided at two frequencies, and the current output from the body through which the current passes is encoded with information regarding the impedance of the body to current at each of those frequencies. To some extent, then, "current" and "signal" are interchangeable, though it should be understood that the type of information encoded in electrical current can take various forms to detect different features of interest.

FIG. 1 is a prior art figure of a monopolar electrosurgical system. The structures of FIG. 1 are embodied in Applicant's commercially-available PLASMABLADE® products. The monopolar device 100 includes an electrosurgical unit (ESU) 102 coupled to a monopolar handpiece 104. The monopolar handpiece 104 is coupled to body 106, which is made up of multiple layers of tissue ($t_1, t_2, \ldots t_n$). Body 106 lies on return pad 108, and electrical current that passes through the body 106 is returned to ESU 102 from the return pad 108.

As indicated by current arrow 110, in a monopolar system the current delivered to body 106 passes through all the layers of tissue ($t_1, t_2, \ldots t_n$) before being returned to the ESU 102 via the return pad 108. The layers of tissue ($t_1, t_2, \ldots t_n$) can each have a corresponding impedance (($Z_1, Z_2, \ldots Z_n$) and, depending on the relative impedances of the layers, power will be dissipated in each layer of tissue ($t_1, t_2, \ldots t_n$). Ensuring that adequate power is delivered to the top layer of the tissue ($t_1$) or potentially the top few layers (e.g., $t_1, t_2$) involves estimating these impedances. Using conventional systems, it is not possible to determine in a conventional monopolar system what the actual impedance of each layer is.

Figure 2:
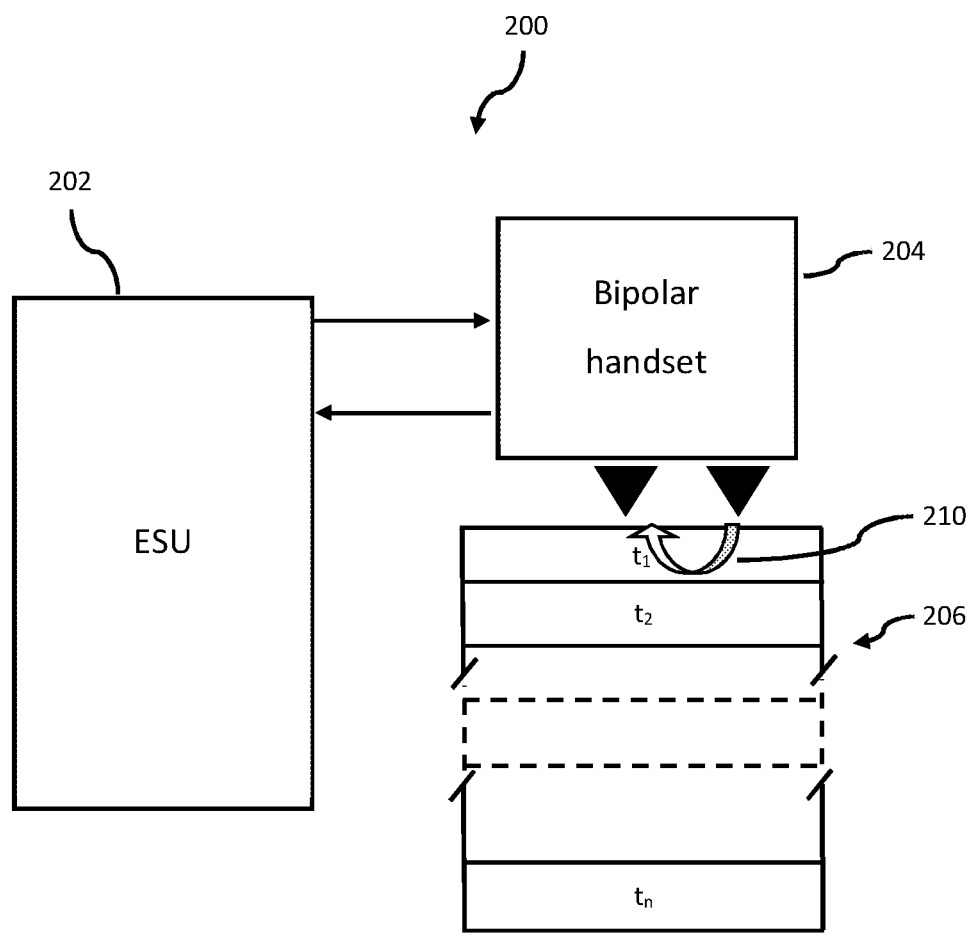
FIG. 2 is a prior art figure of a bipolar electrosurgical system.

FIG. 2 is a prior art figure of a bipolar electrosurgical system 200. In FIG. 2, similar components to those that were previously described with reference to FIG. 1 are given like reference numbers, iterated by 100. Likewise, similar components in the following drawings are also iterated by multiples of 100. A full description of these similar components may be omitted to avoid redundancy herein. Similar components are those the carry out a similar function or have a similar structure, though there may be differences between the various embodiments that will be understood to those of ordinary skill in the art.

Like monopolar electrosurgical system 100 of FIG. 1, bipolar electrosurgical system 200 of FIG. 2 is a system that can provide electrosurgical treatments such as coagulation of bleeding by delivery of heat, or ablation of structures, depending on the power delivered, frequency of the current delivered, and treatment method.

ESU 202 provides power to a bipolar handpiece 204, which delivers power to the body 206 via two tips, as shown by the dual black triangles. Unlike monopolar electrosurgical system 100, there is no return pad in the electrosurgical system 200. Rather, power is delivered to and from the two tips of the handpiece. Accordingly, as indicated by current arrow 210, the depth of current flow is much shallower in electrosurgical system 200. In fact, in many embodiments the majority of the current will pass through a top tissue layer $t_1$ of the series of layers of tissue ($t_1, t_2, \ldots t_n$).

Unlike monopolar electrosurgical system 100 of FIG. 1, the bipolar electrosurgical system 200 of FIG. 2 can be used to determine the impedance of the top tissue layer $t_1$ because the handpiece 204 contacts that layer at two points a set distance apart.

Figure 3:
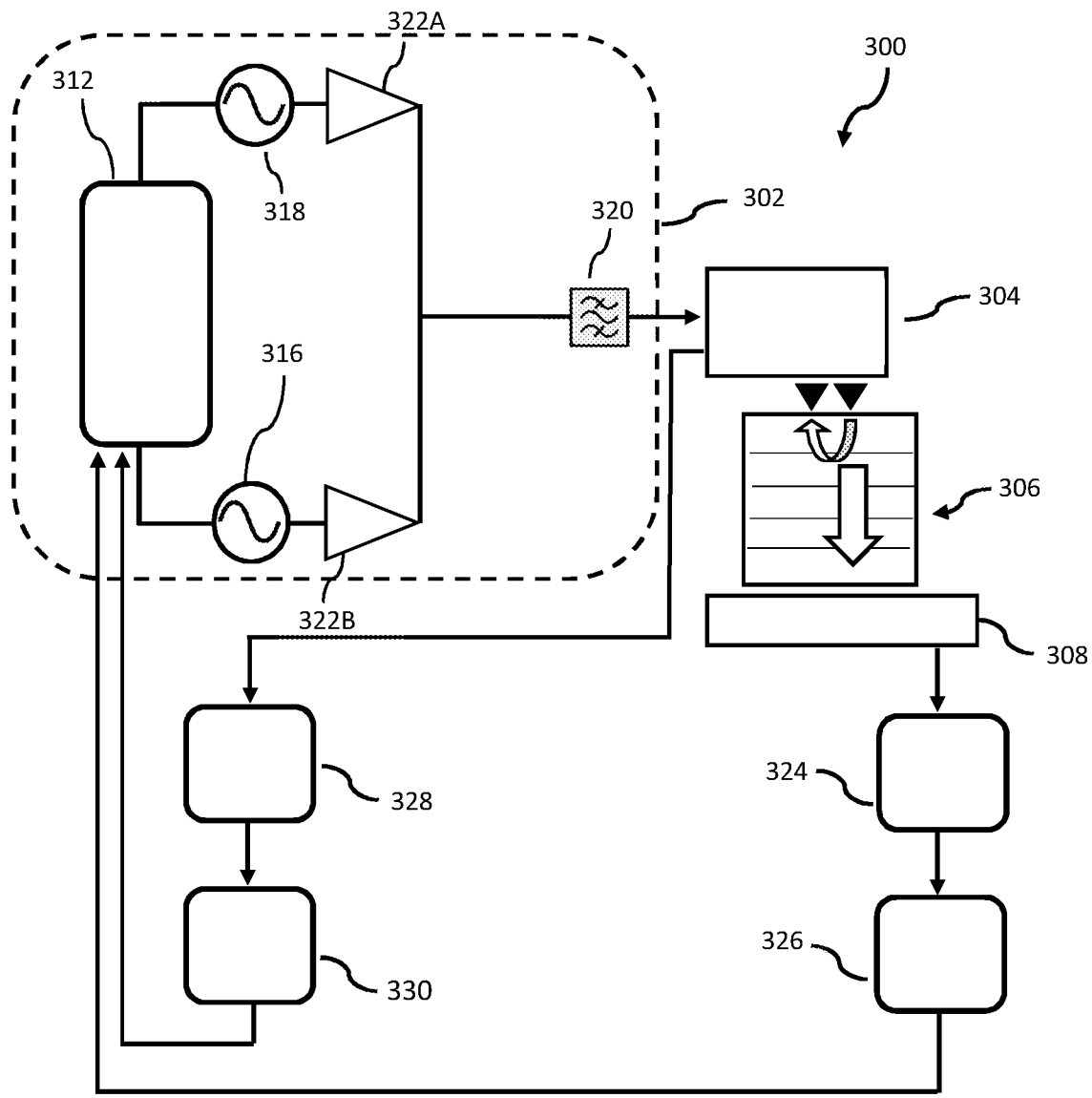
FIG. 3 is a schematic drawing of a monopolar electrosurgical system according to an embodiment.

FIG. 3 is a schematic drawing of a monopolar electrosurgical system 300 according to an embodiment. Electrosurgical system 300 includes ESU 302, monopolar handpiece 304, and return pad 308. Monopolar handpiece 304 and return pad 308 can be used to deliver power through body 306, as indicated by the arrows therein (similar to those shown at FIGS. 1 and 2).

FIG. 3 further depicts a processor 312. Monopolar and bipolar systems such as those shown in FIGS. 1 and 2 may also include processors. However, the processor 312 of FIG. 3 adds functionality not found in such systems. In particular, processor 312 drives two separate power supplies: a first signal source 316 and a second signal source 318. The outputs of these two power supplies (316, 318) are amplified at amplifiers (322A and/or 322B, one or both of which can be present in various embodiments) and combined at diplexer 320.

First signal source 316 and second signal source 318 can drive current at different frequencies, and at different power levels. For example, first signal source 316 can provide a relatively higher power at a relatively high frequency (e.g., about 200 kHz to about 3.3 MHz) that is used to produce an electrosurgical treatment like coagulation of a bleeding tissue or vessel, or ablation of a tissue. Second signal source 318 can then provide a relatively lower power at a relatively lower frequency, relative to the first signal source 316. This second signal source 318 creates a sensing signal that does not meaningfully affect treatment of the body 306 but provides information about the composition of the body 306. The second signal source 318 can provide power at a frequency low enough to pass through the body relatively unimpeded compared to the signal provided by first signal source 316. In general, it is beneficial to use frequencies with a separation therebetween that is high enough (e.g., one octave) to ensure that the signals can be diplexed after passing through the body.

In one embodiment, the treatment power is in the hundreds of watts, while the sensing signal is in the range of mW. Low power for the sensing signal provides the opportunity to use frequency ranges that would not be usable for treatment. For example, the treatment frequency may need to be above 100 kHz to avoid muscle stimulation, while the sensing signal is low enough in power that there it will not cause muscle stimulation even though it is in that range. The voltage at the source can be measured so that the amount of impedance can be determined.

As described above, monopolar systems typically cannot detect the impedance of layers within the body 306, because the signal travels along the entire path from the handpiece to the return pad. In contrast, as shown in FIG. 3 there are two tips on the handpiece 304 as well as a return pad 308. Therefore, as shown by the arrows on body 306, current travels between the tips as well as to the return pad. Dissipation of current of the sensing current produced by the second signal source 318 can therefore be used to determine impedance of the top layer of tissue, $t_1$. Likewise, the amount of dissipation of both sensing and active signals through either the top layer $t_1$ or the entire body 306 can be used to determine impedance or any other frequency-dependent characteristic of the top layer $t_1$ or the entire body 306. That is, using the system depicted in FIG. 3 it is possible to have a bipolar sensing system that at the same time is effectively a monopolar treatment system.

Returned signal from return pad 308 is processed through band-pass filter 324 to transmit the signal from the first signal source 316 while excluding other frequencies. Band-pass filter 324 provides returned signal to a current sense circuit 326 to control the treatment signal power, which in turn passes current to the ESU 300 and the sensed signal to processor 312. In alternative embodiments, current sense circuit 326 can be connected to the return path of the power circuit and can return an analog or digital indication of the quantity of current sensed at current sense circuit 326 to the processor 312. Therefore the system 300 provides the capability of accurate tissue sensing while delivering the treatment energy in electrosurgery. The delivered energy can be adjusted based on the tissue and as a result the risk of overtreatment or undertreatment or the use of inappropriate waveforms can be reduced.

Return signal is also provided from the second tip of the handpiece 314. As shown in FIG. 3, signal is routed to diplexer 328, which separates the signal based on the frequency thereof. The diplexer 328 may include a band-pass filter in the frequency range surrounding that applied by the first signal source 316, while the other output of the diplexer 328 may be created based on a band-pass filter in the frequency range surrounding that applied by the second signal source 318. The separated or diplexed signal is sent to a current sense circuit 330 to determine how much of the signal at each frequency remains after passing through the body 306 (primarily through the top tissue $t_1$). The amount of signal at each frequency is returned to processor 312.

In conventional monopolar systems, there is no way to identify the tissue at the treatment site by using its impedance, since the current flows through the point of treatment and all the different tissues to the return pad. The system described with respect to FIG. 3 resolves this by providing two separate current flow paths, and permitting the detection of impedance at the treatment site on one flow path, while providing treatment on the other flow path.

The ESU 302 is shown in dashed lines in FIG. 3. In embodiments, the various band-pass filters, current sensors, and/or diplexers (324, 326, 328, 330) shown in FIG. 3 can also be a part of the ESU 302. Alternatively, some of these components can be built in to the handpiece 304 or the return pad 308, for example.

Figure 4:
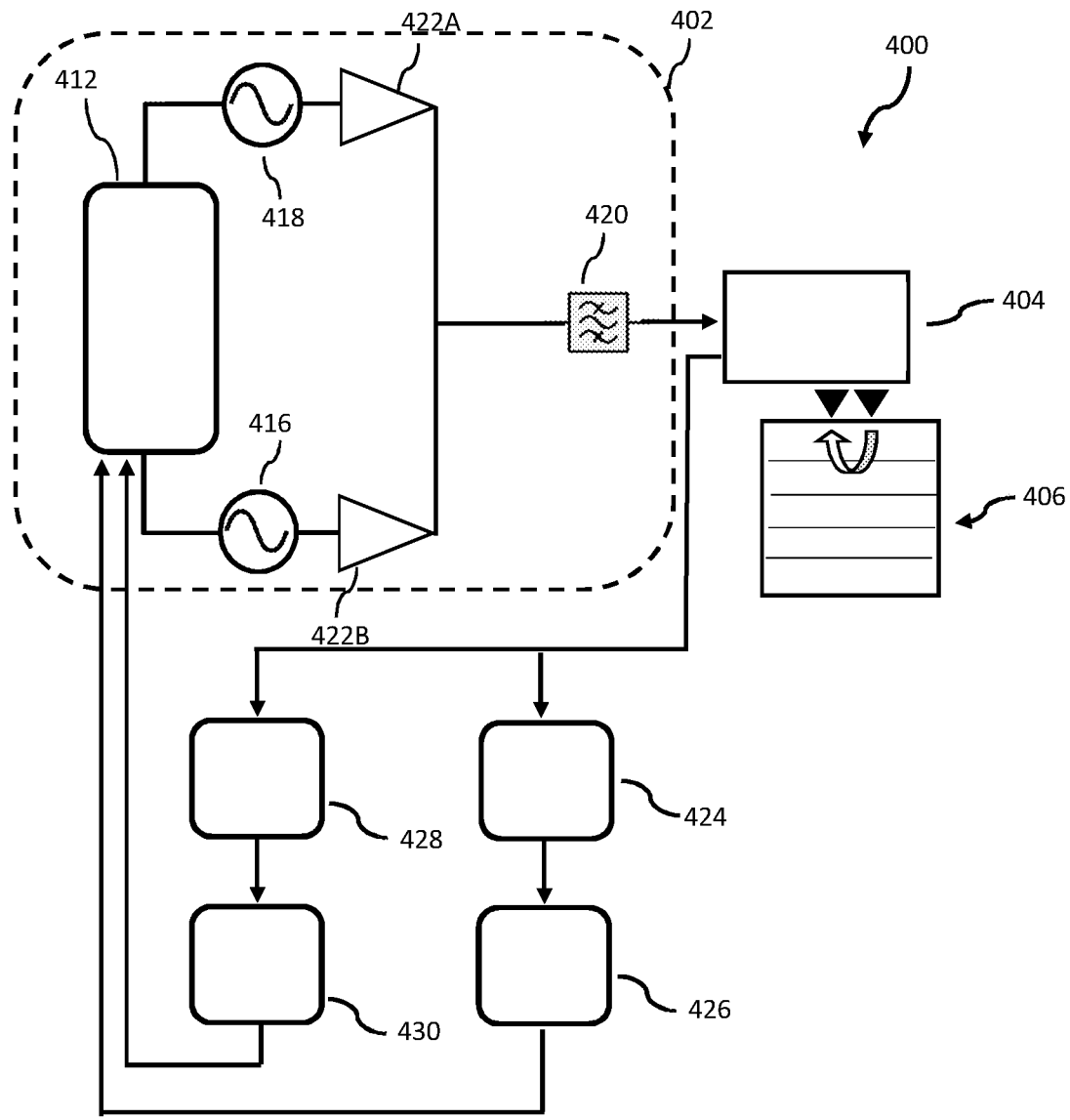
FIG. 4 is a schematic drawing of a bipolar electrosurgical system according to an embodiment.

FIG. 4 is a schematic drawing of a bipolar electrosurgical system 400 according to an embodiment. Like the monopolar system 300 depicted in FIG. 3, bipolar electrosurgical system 400 includes an ESU 402, and a handpiece 404 with two tips that is configured to provide a treatment to a body 406. However, unlike system 300, the bipolar electrosurgical system 400 of FIG. 4 does not include a return pad. Rather, the combined signal from amplifiers (422A and/or 422B, one or both of which can be present in various embodiments) and diplexer 420 (including two different signals at different power levels and frequencies) is delivered from one tip of the handpiece 404 to the other tip and is diplexed at bandpass filters 424 and 428, each of which passes a frequency corresponding to a respective one of the first signal source 416 and the second signal source 418.

Notably, unlike monopolar electrosurgical treatment systems, bipolar electrosurgical devices appear at least superficially to be able to provide signal from one tip to the other and detect the impedance therebetween. However, conventional bipolar electrosurgical devices provide power at a level that is so high and at an inconvenient power and frequency for detection due to high noise level, such that meaningful impedance data is not easily measured. In the system described with respect to FIG. 4, a dedicated second signal at a frequency that is suited for accurate impedance measurement is used in tandem with the first frequency (e.g., one octave apart) that is more appropriate for delivery of the electrosurgical treatment itself.

The amount of current at each frequency level is returned to the ESU 400 and the amount of power is reported to the processor 412, as with the embodiment in FIG. 3. Therefore the system 400 provides the capability of accurate tissue sensing while delivering the treatment energy in electrosurgery. The delivered energy can be adjusted based on the tissue and as a result the risk of overtreatment or undertreatment or the use of inappropriate waveforms can be reduced.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgery system comprising:
an electrosurgical unit (ESU) comprising:
a first signal generator configured to generate an electrical signal at a first frequency;
a second signal generator configured to generate an electrical signal at a second frequency; and
a diplexer configured to combine the electrical signal generated by the first signal generator and the electrical signal generated by the second signal to create a combined signal;
a handpiece including two tips, the handpiece electrically coupled to the diplexer to deliver the combined signal to at least one of the two tips;
a return pad;
a first current-sensing circuit configured to measure a quantity of the electrical signal at the first frequency at the return pad; and
a second current-sensing circuit configured to measure a quantity of the electrical signal at the second frequency at one of the two tips.

2. The electrosurgery system of claim 1, further comprising a processor configured to receive a sensed current from each of the first current-sensing circuit and the second current-sensing circuit.

3. The electrosurgery system of claim 2, wherein the processor is configured to modify a power level of the first signal generator based on the sensed current from each of the first current-sensing circuit and the second current-sensing circuit.

4. The electrosurgery system of claim 1, wherein the first current-sensing circuit and the second current-sensing circuit are each a part of the ESU.

5. An electrosurgery system comprising:
an electrosurgical unit (ESU) comprising:
a first signal generator configured to generate an electrical signal at a first frequency;
a second signal generator configured to generate an electrical signal at a second frequency; and
a first diplexer configured to combine the electrical signal generated by the first signal generator and the electrical signal generated by the second signal to create a combined signal;
a handpiece including two tips, the handpiece electrically coupled to the first diplexer to deliver the combined signal to at least one of the two tips;
a second diplexer coupled to at least one of the two tips;
a first current-sensing circuit configured to measure a quantity of the electrical signal at the first frequency at one of the two tips; and
a second current-sensing circuit configured to measure a quantity of the electrical signal at the second frequency at one of the two tips.

6. The electrosurgery system of claim 5, further comprising a processor configured to receive a sensed current from each of the first current-sensing circuit and the second current-sensing circuit.

7. The electrosurgery system of claim 6, wherein the processor is configured to modify a power level of the first signal generator based on the sensed current from each of the first current-sensing circuit and the second current-sensing circuit.

8. The electrosurgery system of claim 5, wherein the first current-sensing circuit and the second current-sensing circuit are each a part of the ESU.

* * * * *